(12) United States Patent
Chikami et al.

(10) Patent No.: US 8,272,867 B2
(45) Date of Patent: Sep. 25, 2012

(54) ORTHODONTIC DEVICE

(76) Inventors: Kunio Chikami, Kochi (JP); Rohit C L Sachdeva, Plano, TX (US)

( * ) Notice: Subject to any disclaimer, the term of this patent is extended or adjusted under 35 U.S.C. 154(b) by 0 days.

(21) Appl. No.: 11/996,090

(22) PCT Filed: Jul. 14, 2006

(86) PCT No.: PCT/JP2006/314064
§ 371 (c)(1),
(2), (4) Date: Jan. 18, 2008

(87) PCT Pub. No.: WO2007/010856
PCT Pub. Date: Jan. 25, 2007

(65) Prior Publication Data
US 2009/0130621 A1    May 21, 2009

(30) Foreign Application Priority Data
Jul. 20, 2005 (JP) ................ 2005-209524

(51) Int. Cl.
*A61C 3/00* (2006.01)
(52) U.S. Cl. ........................................... 433/10
(58) Field of Classification Search ............ 433/8–18
See application file for complete search history.

(56) References Cited

U.S. PATENT DOCUMENTS

| 4,077,126 A * | 3/1978 | Pletcher ............... 433/10 |
| 4,371,337 A * | 2/1983 | Pletcher ............... 433/10 |
| 4,419,078 A | 12/1983 | Pletcher |
| 4,551,094 A * | 11/1985 | Kesling ............... 433/8 |
| 4,559,012 A * | 12/1985 | Pletcher ............... 433/10 |
| 4,655,708 A * | 4/1987 | Fujita ............... 433/10 |
| 5,094,614 A * | 3/1992 | Wildman ............... 433/14 |
| 5,224,858 A * | 7/1993 | Hanson ............... 433/10 |
| 5,322,435 A | 6/1994 | Pletcher |
| 2002/0110773 A1 * | 8/2002 | Abels et al. ............... 433/10 |
| 2005/0255422 A1 * | 11/2005 | Cordato ............... 433/10 |

FOREIGN PATENT DOCUMENTS

| JP | 59-103658 | 6/1984 |
| JP | 4-309346 | 10/1992 |
| JP | 3512466 | 1/2004 |

* cited by examiner

*Primary Examiner* — Heidi M Eide

(57) ABSTRACT

An orthodontic device consisting of a bracket having a slot formed by arm parts facing each other in the vertical direction, and an inner part having a socket for holding a wire. The orthodontic device is characterized in that the opening of the slot is closed by inserting the inner part into the slot so that the inner part can be held by the arm parts. Different torque depending on the socket can be applied to a tooth. A desired torque can be applied by only changing the inner part without changing the bracket.

4 Claims, 12 Drawing Sheets

--Prior Art--

--Prior Art--

ORTHODONTIC DEVICE

FIELD OF THE INVENTION

The present invention relates to an orthodontic device.

DESCRIPTION OF THE RELATED ART

A conventional orthodontic device includes a bracket having a horizontal groove 72 into which a wire 80 is inserted and a vertical groove 73 formed in the front part thereof and a thin-plate-like slide member 71 inserted in the vertical groove 73 (see FIGS. 11 and 12 and the Patent Document 1). The slide member 71 can move vertically along the vertical groove 73, and the slide member 71 is moved downwardly to close the horizontal groove 72, thereby holding the wire 80 therein.

Patent Document 1: Japanese Patent Publication No. 3512466 B

However, the slide member 71 is a thin plate and therefore is inferior in strength. In addition, most of the front surface of the slide member 71 is exposed, and therefore, the slide member 71 is likely to be subjected to an external force and can be damaged when subjected to the external force.

In addition, the slide member 71 has a shallow recess 74 formed in the back surface thereof, the bracket has a short protrusion 75 formed on the front surface thereof, and the recess 74 and the protrusion 75 are lightly engaged with each other. Therefore, there is a possibility that the slide member 71 is disengaged from and comes off the bracket when the slide member 71 is subjected to an external force. If the slide member 71 comes off the bracket, the wire 80 cannot be held in the bracket.

To minimize the possibility of the slide member 71 coming off, a spring member can be used to keep the slide member 71 engaged with the bracket by the action of the resilient force. However, the spring member incorporated in the bracket extends along the depth, so that the structure is undesirably complicated (see FIG. 18 of the Patent Document 1).

SUMMARY OF THE INVENTION

Thus, an object of the present invention is to provide an orthodontic device capable of holding a wire with a simple, not complicated, structure.

In order to attain the object, according to the present invention, there is provided an orthodontic device, including: a bracket having a slot defined by an upper arm portion and a lower arm portion facing each other; and an inner part having a socket for holding a wire, in which the inner part is inserted into the slot to be held between the upper arm portion and the lower arm portion, thereby closing an opening of the slot.

With such a configuration, the wire can be held with reliability with a simple structure in which the inner part having the socket is inserted into the slot formed in the bracket. Since the structure is simple, the orthodontic device is easy to handle in treatment and can be reduced in size. Furthermore, since the inner part is held between the upper and lower arm portions facing each other, the inner part is inserted stably, so that the opening of the slot is stably kept closed, and the wire can be held with reliability. Furthermore, since the inner part has a shape suitable for insertion into the slot defined by the upper and lower arm portions facing each other, the inner part has a sufficient strength.

In the orthodontic device according to the present invention, the socket of the inner part may be angled. More specifically, the orthodontic device may be characterized in that the direction of opening of the socket of the inner part is angled.

With such a configuration, different torque depending on the angle of the direction of opening of the socket can be applied to a tooth. When applying a torque, if a plurality of inner parts having differently angled sockets are prepared, a desired torque can be applied only by changing the inner part without changing the bracket, which is quite preferable. In addition, the treatment can be performed easily, and the treatment time can be reduced.

Angling the direction of opening of the socket means angling the perpendicular passing through the center of the socket with respect to the perpendicular passing through the center of the base part of the inner part.

Furthermore, in the orthodontic device according to the present invention, the inner part may have a handle part.

The slot and the inner part are difficult to handle in treatment because of their small sizes. However, if the inner part is provided with the handle part, the inner part can be handled by holding the handle part. As a result, the inner part can be easily handled, and the treatment can be easily performed.

Thus, an orthodontic device capable of holding a wire with a simple, not complicated, structure is provided.

Figure 1:
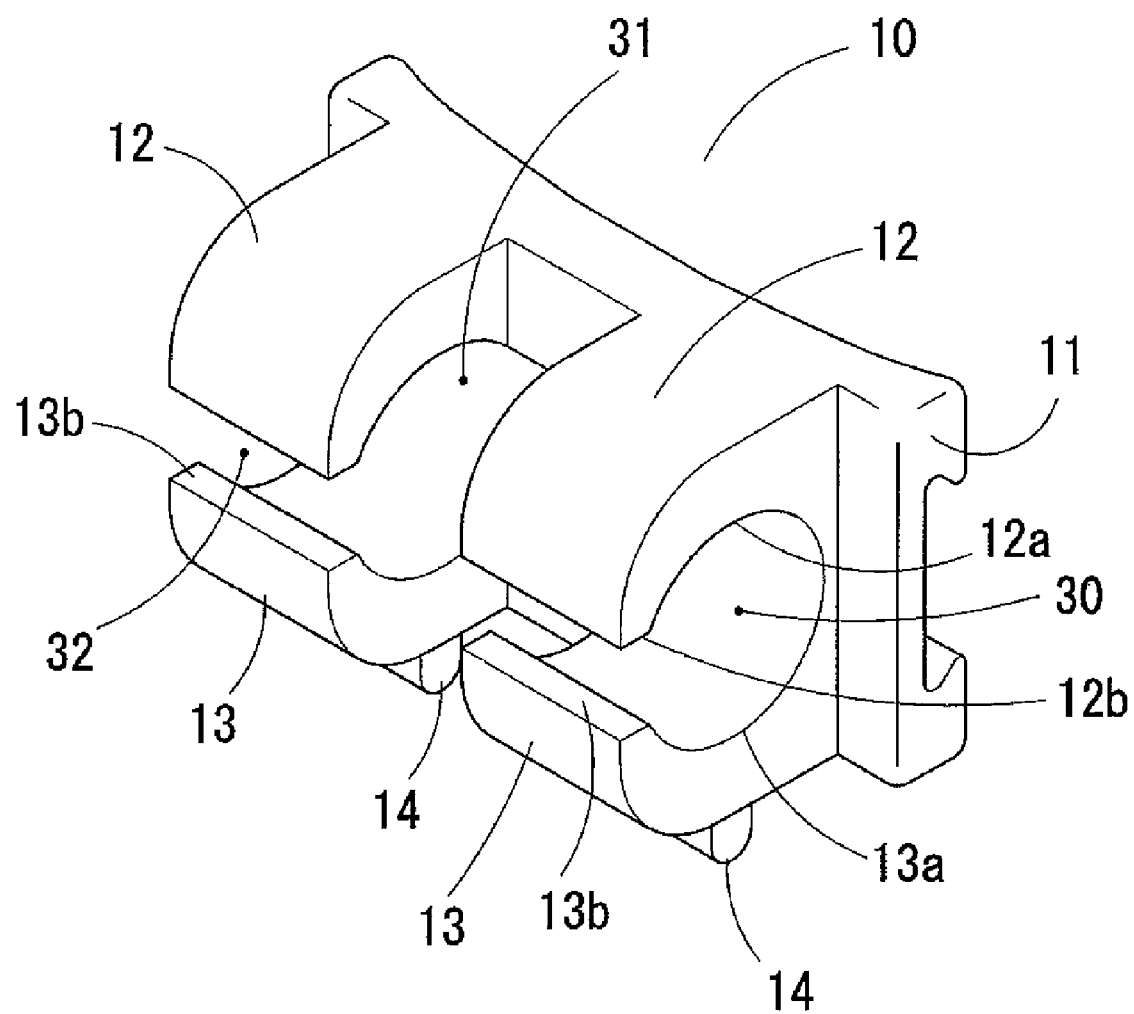
FIG. 1 is a perspective view of a bracket according to embodiments 1 and 2 of the present invention.

DESCRIPTION OF REFERENCE NUMERALS 10 bracket
12 upper arm portion
13 lower arm portion
20 inner part
22 handle part
24 socket
30 slot
32 opening of slot 40, 60 wire

DETAILED DESCRIPTION OF THE PREFERRED EMBODIMENTS

In the following, best modes for carrying out the present invention will be described with reference to the drawings showing embodiments of the present invention. FIGS. 1 to 10 show orthodontic devices according to embodiments of the present invention.

Embodiment 1

FIGS. 1 to 4 show an embodiment 1.

An orthodontic device according to the embodiment 1 includes a bracket 10 and an inner part 20 inserted in the bracket 10.

Referring to FIG. 1, the bracket 10 has a base portion 11 that is to be attached to the tooth surface, an upper arm portion 12 extending forward from a front surface of the base portion 11, and a lower arm portion 13 extending forward from the front surface of the base portion 11.

The base portion 11 is intended to be attached to the tooth surface with an adhesive or the like and has a protrusion, which aids in attachment of the bracket 10 to the tooth surface, on the back surface thereof.

The upper arm portion 12 and the lower arm portion 13 form a slot 30, in which the inner part 20 is inserted. Specifically, an arc-shaped surface 12a of the upper arm portion 12 and an arc-shaped surface 13a of the lower arm portion facing each other form the slot 30, which is a space having a substantially cylindrical shape.

Figure 3:
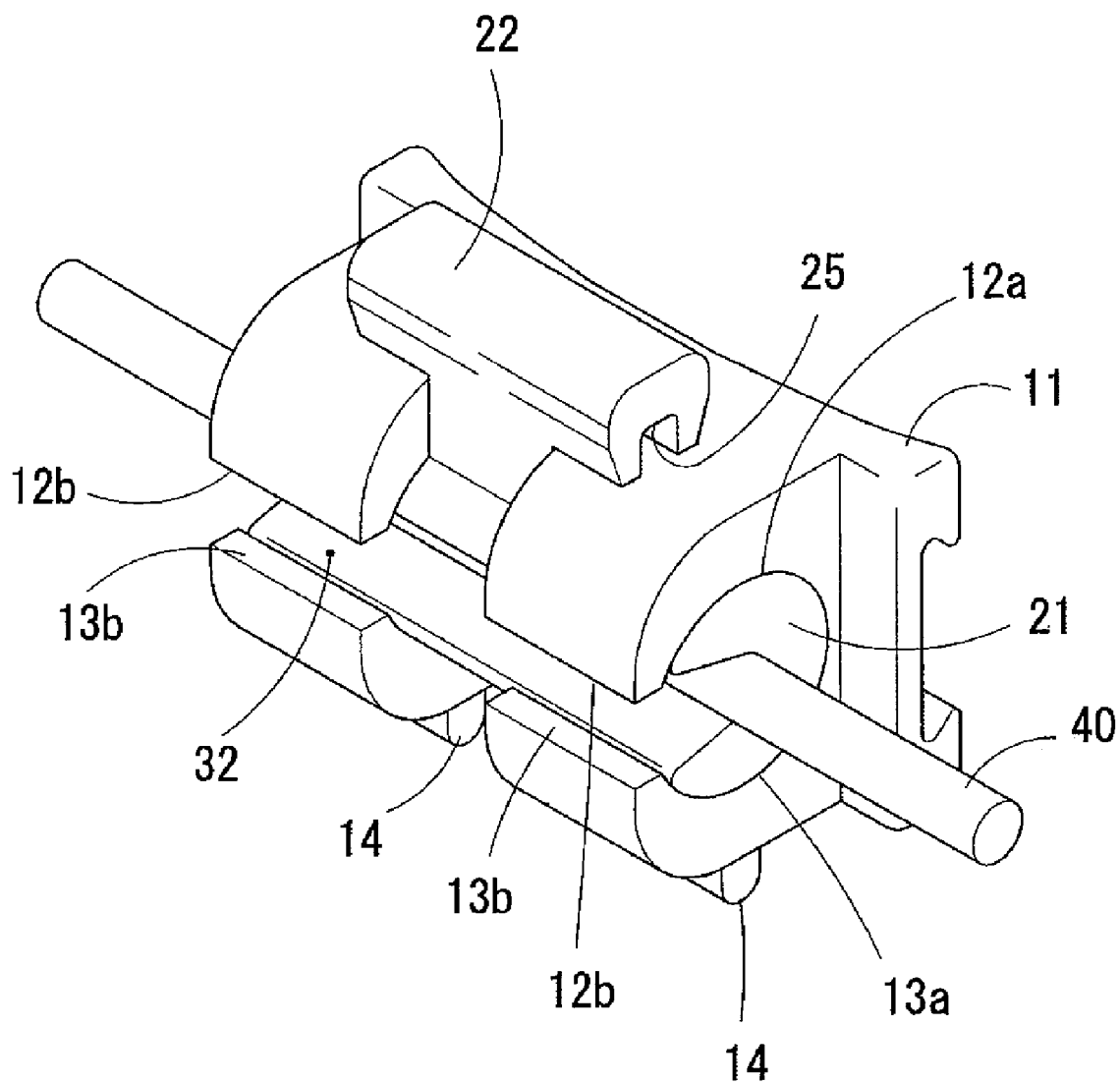
FIG. 3 is a perspective view of the inner part inserted in the bracket in the embodiment 1 of the present invention.

The upper arm portion 12 has the shape of a hook, and the tip part of the upper arm portion 12 is curved to cover the outer perimeter of the inner part 20, as shown in FIG. 3. Similarly, the lower arm portion 13 has the shape of a hook, and the tip part of the lower arm portion 13 is curved to cover the outer perimeter of the inner part 20. Specifically, most of the lower surface of the upper arm portion 12 is constituted by the semicircular arc-shaped surface 12a, most of the upper surface of the lower arm portion 13 is constituted by the semicircular arc-shaped surface 13a, and the two surfaces facing each other define the substantially cylindrical slot 30. When the inner part 20 is inserted in the slot 30, the inner part 20 is held between the arc-shaped surface 12a of the upper arm portion 12 and the arc-shaped surface 13a of the lower arm portion 13. The horizontal width of the slot 30 and the horizontal width of the inner part 20 are substantially equal to each other.

The slot 30 thus configured stably holds the inner part 20, and therefore, the possibility of the inner part 20 coming off the bracket 10 is reduced compared with the example of the related art described earlier. In addition, the front surface of the inner part 20 is less exposed compared with the example of the related art described earlier, and therefore, the inner part 20 is less affected by external forces and less susceptible to damage.

The upper arm portion 12 has a flat surface 12b at the tip end thereof. The lower arm portion 13 also has a flat surface 13b at the tip end thereof. The flat surface 12b of the upper arm portion 12 and the flat surface 13b of the lower arm portion 13 face each other and define an opening 32 of the slot 30. The opening 32 is a space that allows horizontal movement of a joint part 23 of the inner part 20. In addition, the opening 32 helps to insert a wire 40 into the slot 30. The vertical width of the opening 32 is substantially equal to the thickness (d) of the joint part 23.

The upper arm portion 12 and the lower arm portion 13 have a vertical slit 31 formed at the horizontal center thereof. Specifically, the upper arm portion 12 and the lower arm portion 13 have the vertical slit 31, which is a vertical notch formed to divide each of the arm portions in two. The vertical slit 31 is a space that allows vertical movement of the joint part 23 of the inner part 20. The horizontal width of the vertical slit 31 is substantially equal to the horizontal width (W) of the joint part 23.

Figure 2:
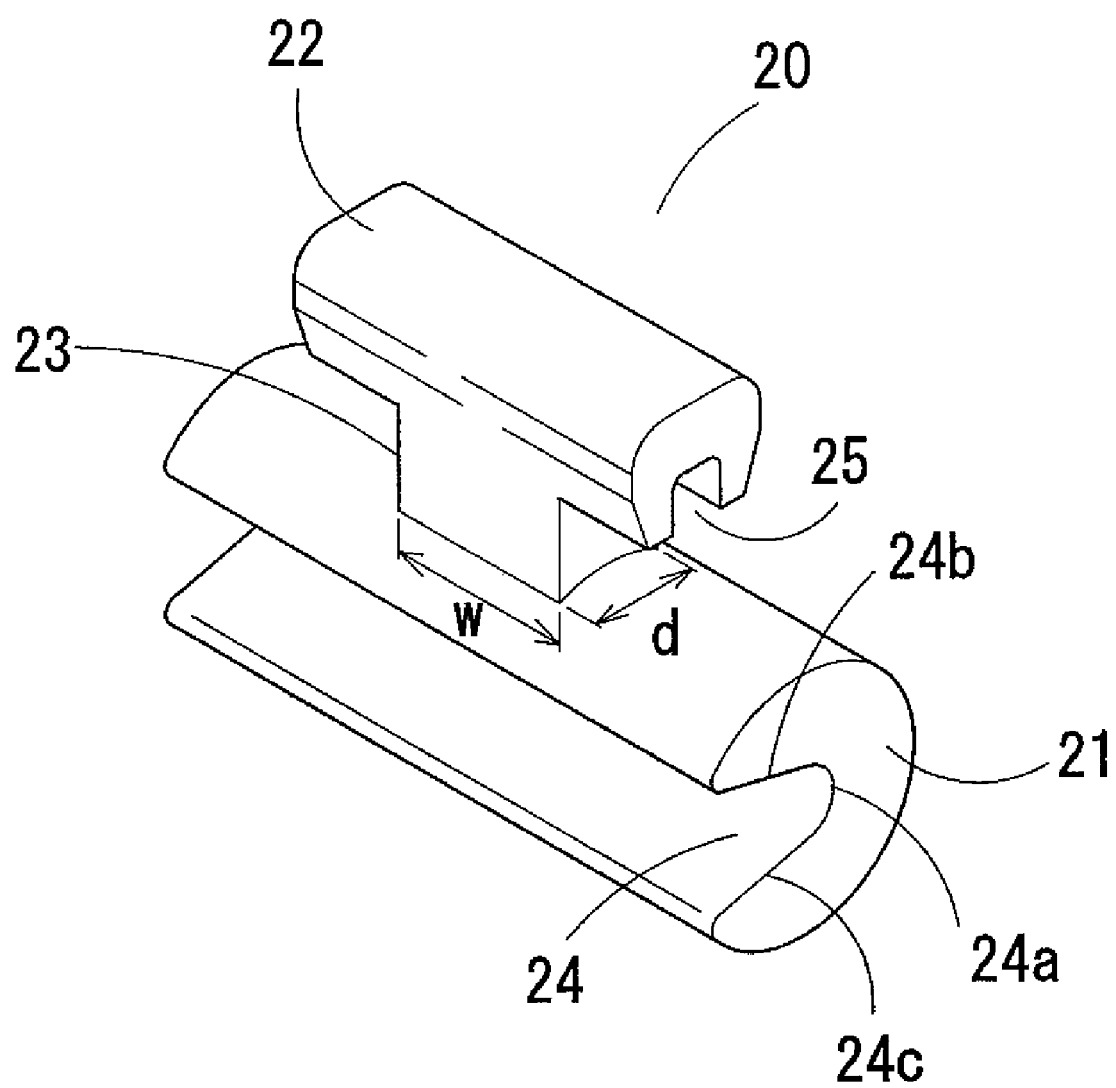
FIG. 2 is a perspective view of an inner part according to the embodiment 1 of the present invention.

Referring to FIG. 2, the inner part 20 to be inserted into the slot 30 has a base part 21, a handle part 22, and the joint part 23 that couples the base part 21 and the handle part 22 to each other.

The base part 21, which is to be inserted into the slot 30, is shaped to conform to the shape of the slot 30. That is, the base part 21 is shaped so that the base part 21 can be fitted into the slot 30. In this embodiment, the slot 30 has a substantially cylindrical shape, and therefore, the base part 21 of the inner part 20 has a substantially cylindrical shape with a notch formed therein. The inner part 20 having such a shape has a higher section modulus and a higher strength than the thin-plate-like slide member of the example of the related art described earlier. Therefore, the inner part 20 is less susceptible to damage even if an external force is applied thereto.

The base part 21 is intended for holding the wire 40 and has a socket 24 for holding the wire 40 having a circular cross section. The socket 24 is formed by cutting a part of the base part 21 to form a space for housing the wire 40 in the base part 21. In this embodiment, the base part 21 having the socket 24 has a substantially C-shaped cross section and has an outward opening. Specifically, the socket 24 is defined by a bottom part 24a and side surfaces 24b and 24c, the bottom part 24a is an arc-shaped surface, and the side surfaces 24b and 24c are flat surfaces. The side surfaces 24b and 24c are inclined and diverge outwardly to form the opening. The wire 40 is inserted into the opening.

The handle part 22 is coupled to the base part 21. Specifically, the joint part 23 is connected to the outer perimeter of the base part 21 at one end and to the handle part 22 at the other end. The handle part 22 has a recess 25 formed therein. The recess 25 opens toward the joint part 23 and is engaged with a protrusion 14 formed on the back surface of the lower arm portion 13 when the handle part 22 is rotated downwardly.

The bracket 10 and the inner part 20 are each configured as described above. The two components are assembled as described below.

The inner part 20 and the slot 30 are placed side by side so that the arc-shaped outer perimeter of the inner part 20 and the arc-shaped surfaces 12a and 13a of the slot 30 are aligned with each other, and the opening 32 of the slot 30 and the joint part 23 are aligned each other. Then, the inner part 20 is moved horizontally and inserted into the slot 30. When the joint part 23 enters the vertical slit 31, the horizontal movement of the inner part 20 is stopped, and the inner part 20 is rotated by vertically moving the handle part 22. Then, as shown in FIG. 3, the opening 32 and the opening of the socket 24 of the inner part 20 are substantially aligned with each other. In this state, when the wire 40 is inserted into the opening 32, the wire 40 reaches to the bottom part 24a of the socket 24 because the opening 32 and the opening of the socket 24 are aligned with each other.

Figure 4:
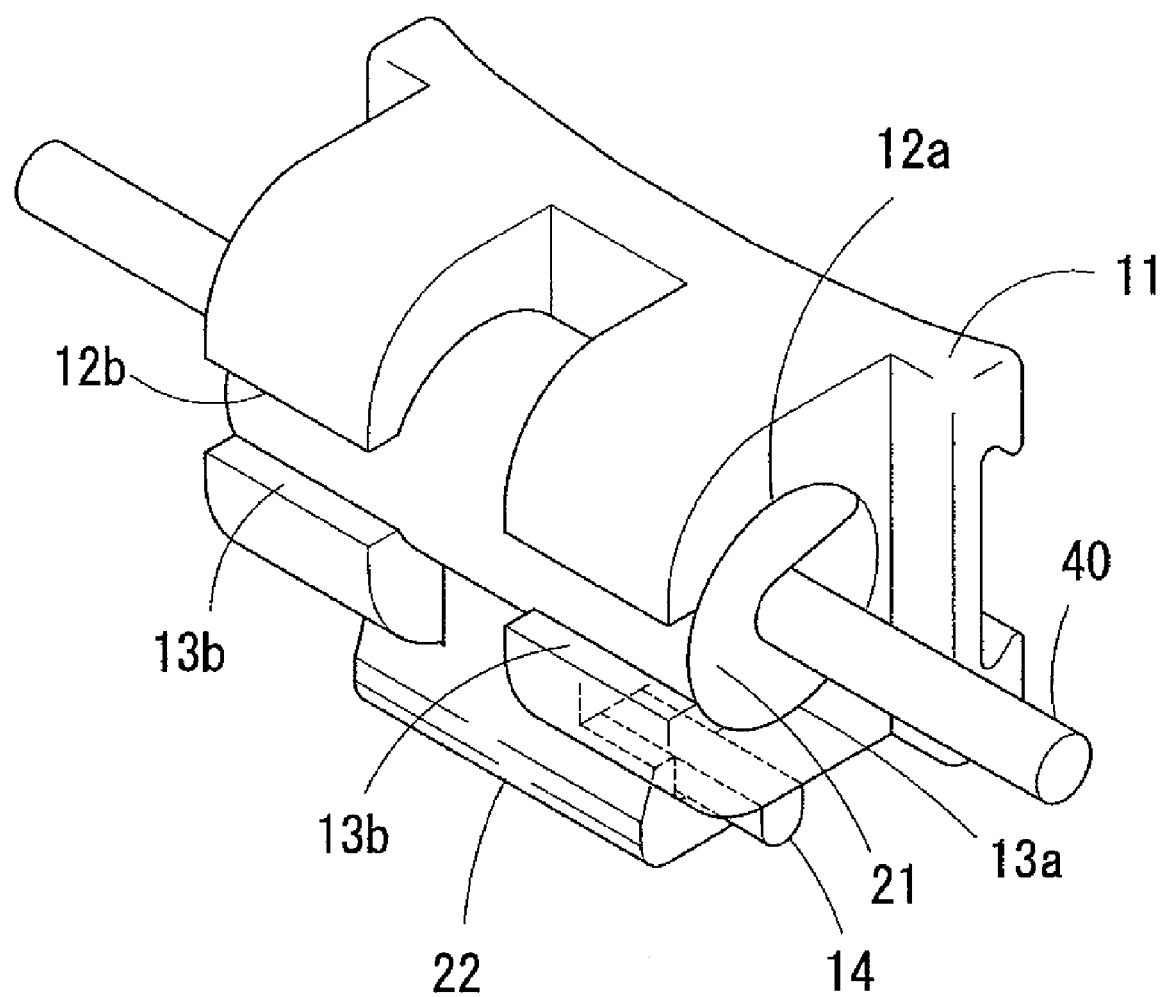
FIG. 4 is a perspective view of the inner part inserted in the bracket in the embodiment 1 of the present invention.

Once the wire 40 is inserted into the socket 24, the handle part 22 is moved downwardly to rotate the inner part 20 again. As the inner part 20 rotates, the opening of the socket 24 moves away from the opening 32 of the slot 30, and the two openings become displaced from each other. Thus, as shown in FIG. 4, the opening 32 is closed with a part of the inner part 20 other than the socket 24 (the part opposite to the socket 24). In this way, the wire 40 is held in the bracket 10.

At this time, the recess 25 in the handle part 22 is engaged with the protrusion 14 on the lower arm portion 13 to help keep the wire 40 held in the inner part 20. Since the joint part 23 is positioned in the vertical slit 31, the inner part 20 is prevented from moving horizontally. In this way, the wire 40 is held with higher reliability.

In the above description, the wire 40 is inserted after the inner part 20 is fitted into the bracket 10. Alternatively, of course, the wire 40 can be inserted before the inner part 20 is inserted into the bracket 10.

The bracket 10 and the inner part 20 are made of a dental metal, a synthetic material, a ceramic or a synthetic resin, for example. Examples of the synthetic resin include polymethyl methacrylate, polyoxymethylene, polycarbonate, polypropylene, polyethylene and polyethylene naphthalate. Many conventional orthodontic devices use metals for strength reasons. However, the orthodontic device according to the present invention has a simple structure and therefore can be reduced in size while maintaining a sufficient strength, so that the orthodontic device need not be made of a metal and can be made of a plastic or ceramic. Furthermore, since the orthodontic device has a simple structure and therefore can be reduced in size as described above, the orthodontic device is inconspicuous when attached to the teeth surface and is aesthetically pleasing. Thus, the orthodontic device puts reduced psychological and physical burdens on patients and therefore is preferable.

The bracket 10 has a width of about 2.8 to 3.5 mm, a height of about 2.5 mm and a depth of about 2.0 mm. The base portion 11 has a thickness of 0.45 mm, and the upper (lower) arm portion has a thickness (in the vertical direction) of about 0.1 mm at the base end thereof and a thickness (in the vertical direction) of about 0.25 mm at the tip end thereof. The vertical slit has a horizontal width of about 0.8 mm, and the opening 32 of the slot 30 has a vertical width of 0.7 mm. The cylindrical slot 30 has a diameter of about 1.3 mm and has a horizontal length of about 2.5 to 3.2 mm. The substantially cylindrical base part 21 of the inner part 20 has a diameter of about 1.3 mm, and the joint part has a thickness (d) of about 0.7 mm and a horizontal width (W) of about 0.8 mm. The depth of the groove of the socket is about 0.9 mm. The wire 40 has a diameter of about 0.012 to 0.020 inch.

Embodiment 2

FIGS. 1 and 5 to 10 show an embodiment 2 of the present invention.

An orthodontic device according to the embodiment 2 includes a bracket 10 and an inner part 50. The bracket 10 in the embodiment 2 has the same structure as in the embodiment 1, but the inner part 50 has different structure.

Figure 5:
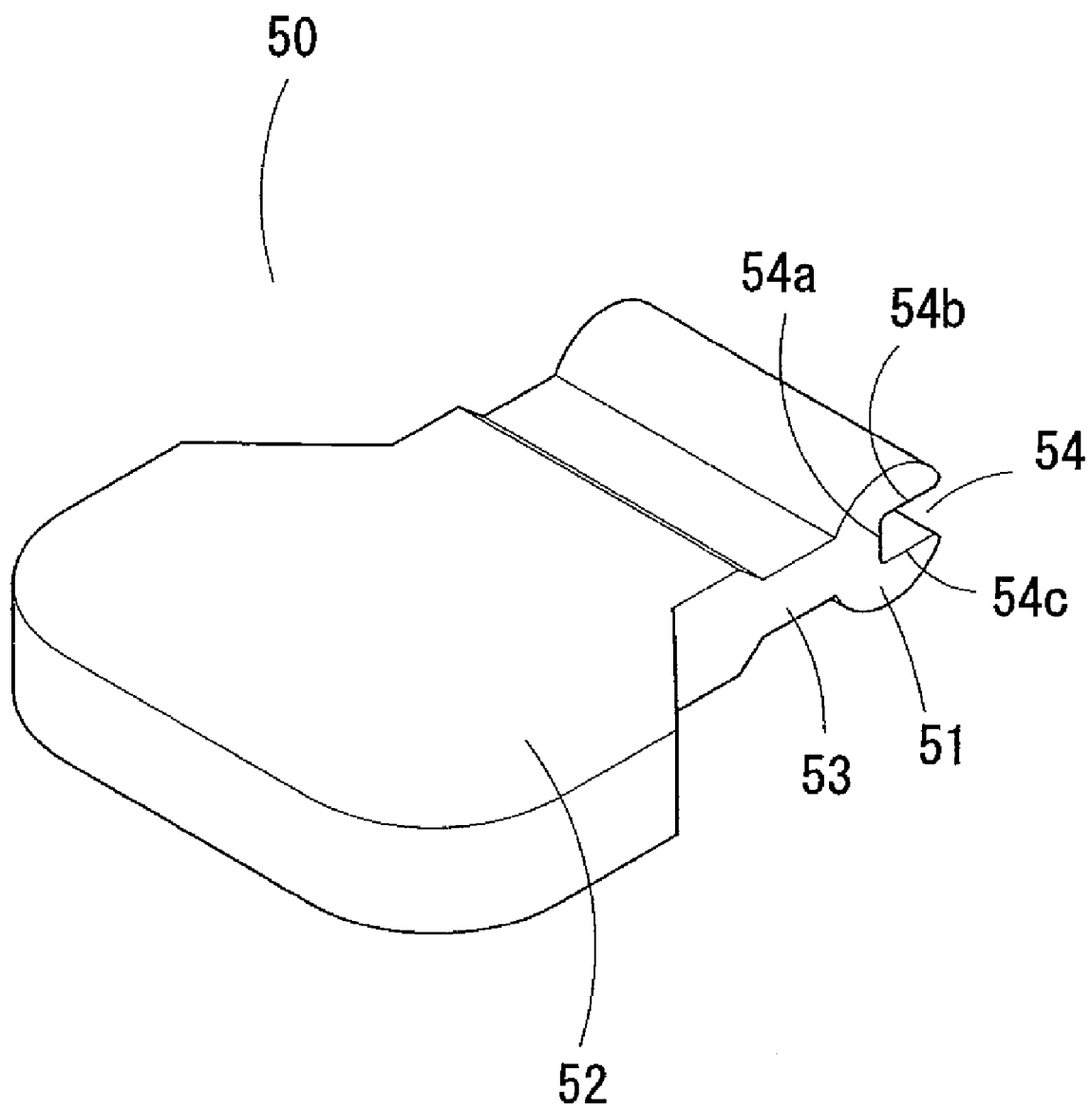
FIG. 5 is a perspective view of an inner part according to the embodiment 2 of the present invention.

As shown in FIG. 5, the inner part 50 has a base part 51, a handle part 52 and a joint part 53. The base part 51 is to be inserted into a slot 30 and therefore shaped to conform to the shape of the slot 30. In this embodiment, the slot 30 has a substantially cylindrical shape, and therefore, the base part 51 also has a substantially cylindrical shape with a notch formed therein. The notch formed in the base part 51 constitutes a socket 54 for holding a wire 60 having a rectangular cross section. The socket 54 is shaped to conform to the rectangular shape of the wire 60. Specifically, referring to FIG. 8 and the like, the socket 54 is defined by opposite side surfaces 54b and 54c and a bottom surface 54a perpendicular to the side surfaces 54b and 54c. In the embodiment 2, the cross section of the wire can be any polygon and is not limited to the shape described in this embodiment and shown in the drawings.

Figure 8:
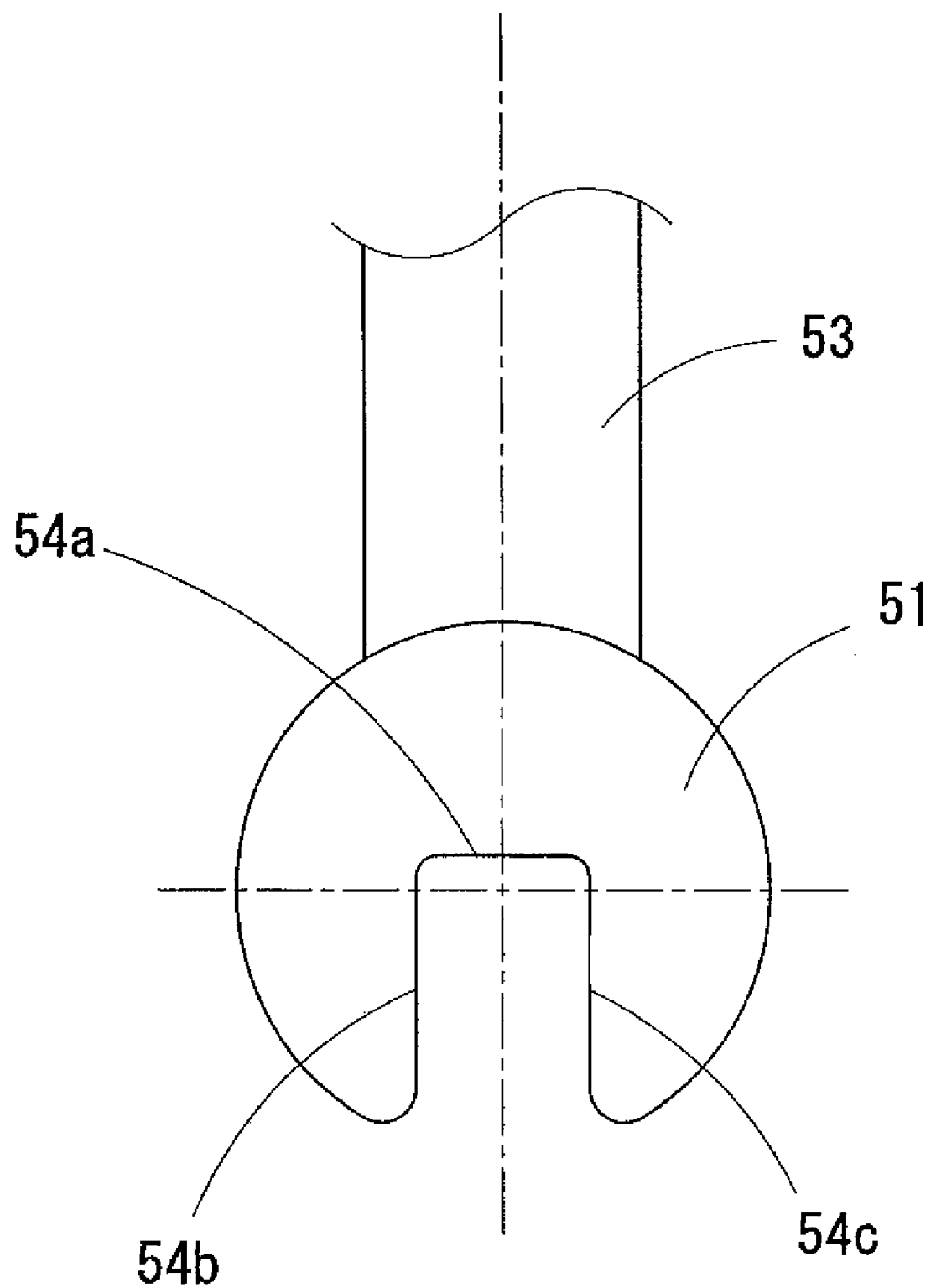
FIG. 8 is a perspective view of the inner part (the angle of opening equals to 0 degrees) according to the embodiment 2 of the present invention.
Figure 9:
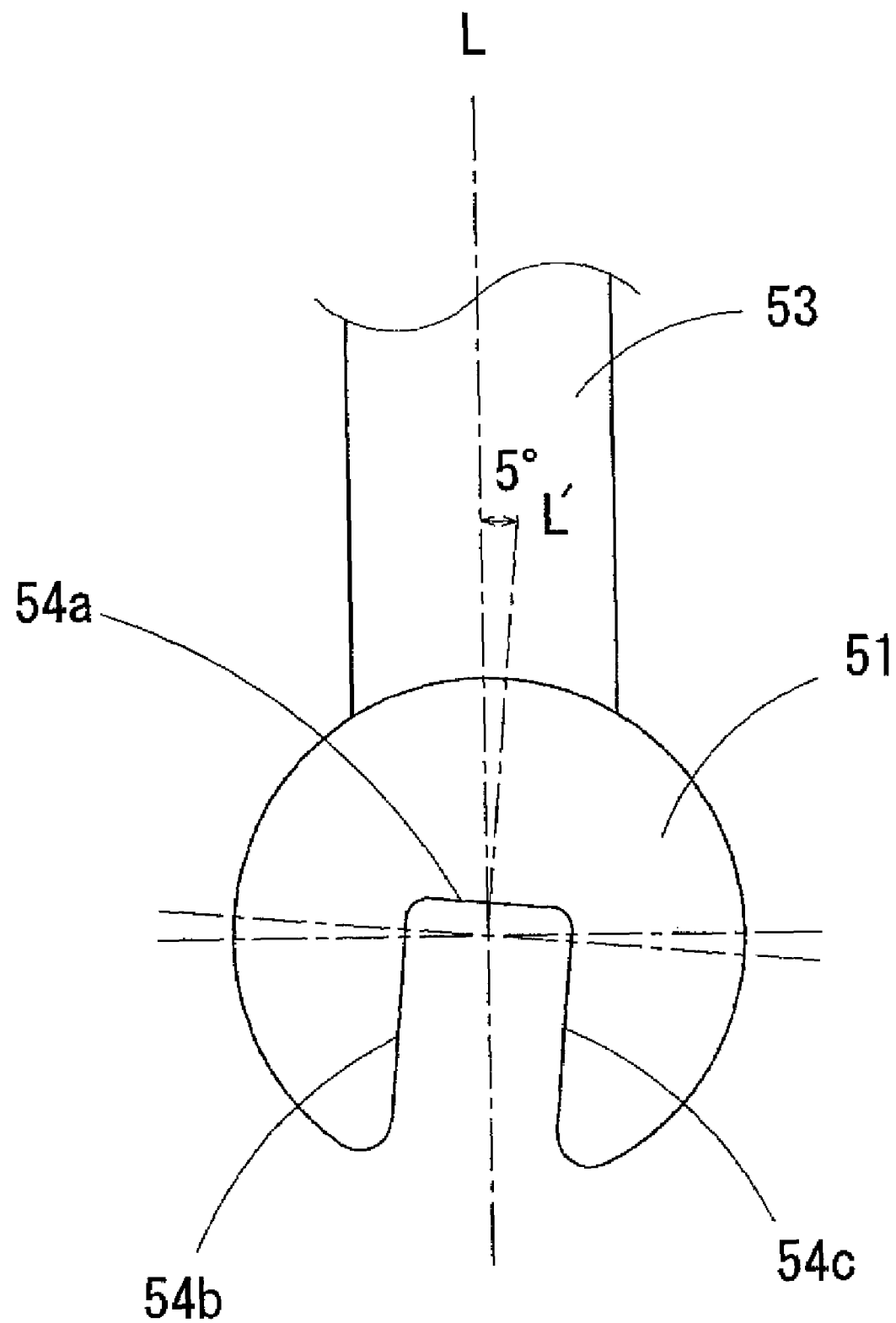
FIG. 9 is a perspective view of the inner part (the angle of opening equals to 5 degrees) according to the embodiment 2 of the present invention.
Figure 10:
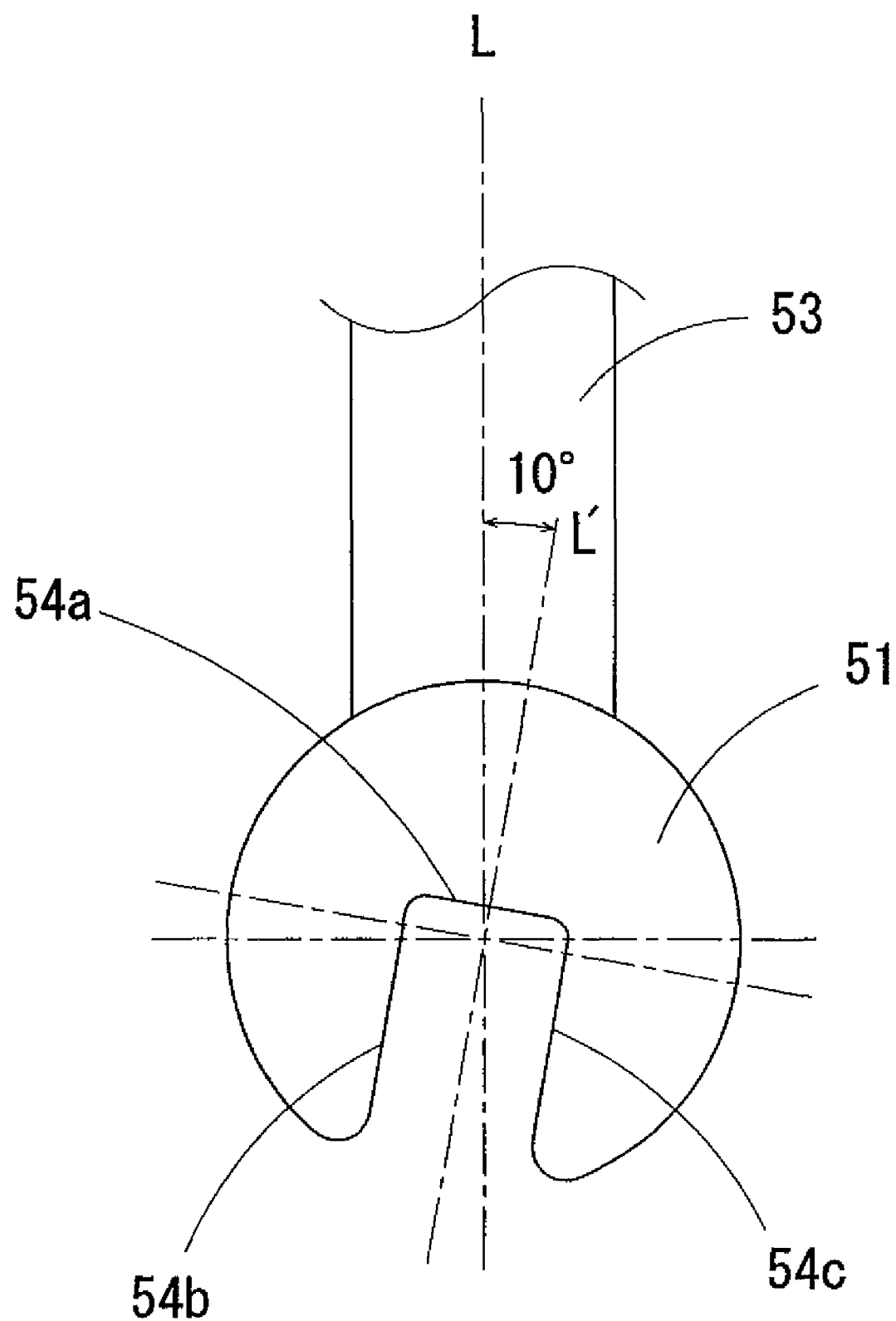
FIG. 10 is a perspective view of the inner part (the angle of opening equals to 10 degrees) according to the embodiment 2 of the present invention.
Figure 11:
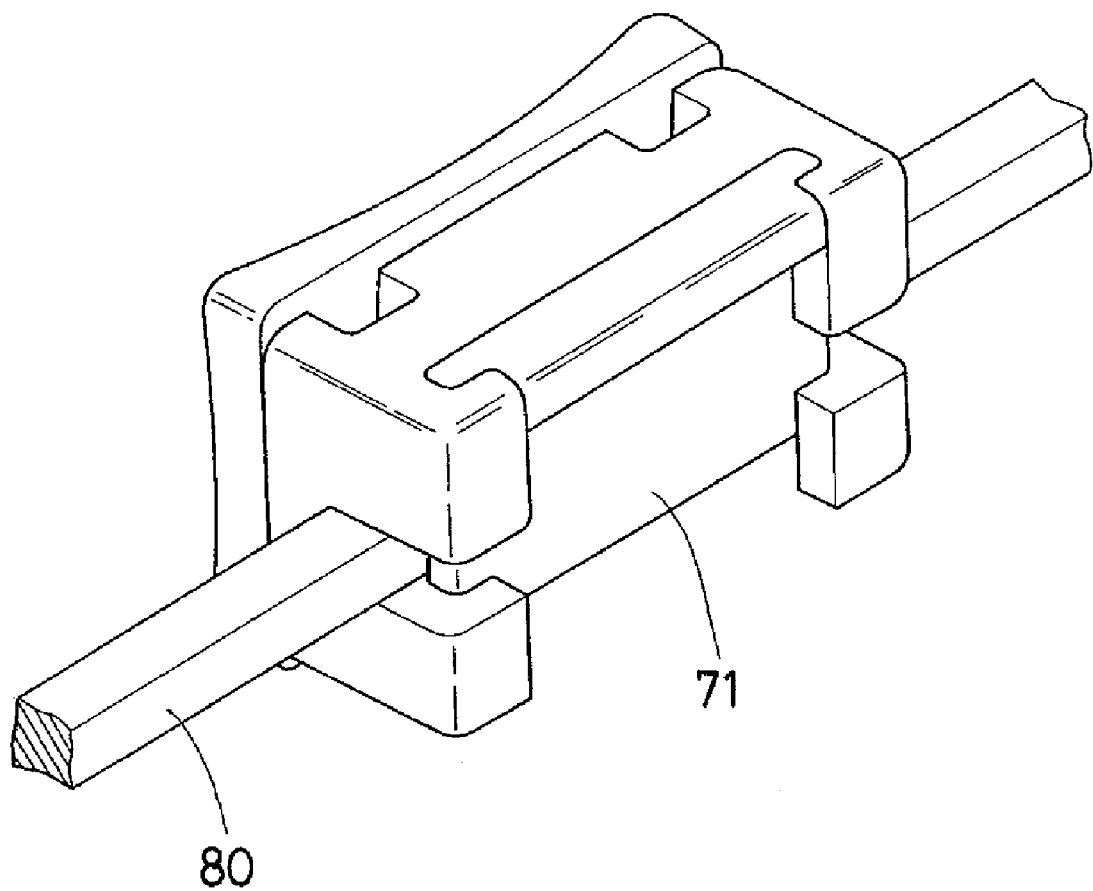
FIG. 11 is a perspective view of an example of the related art.
Figure 12:
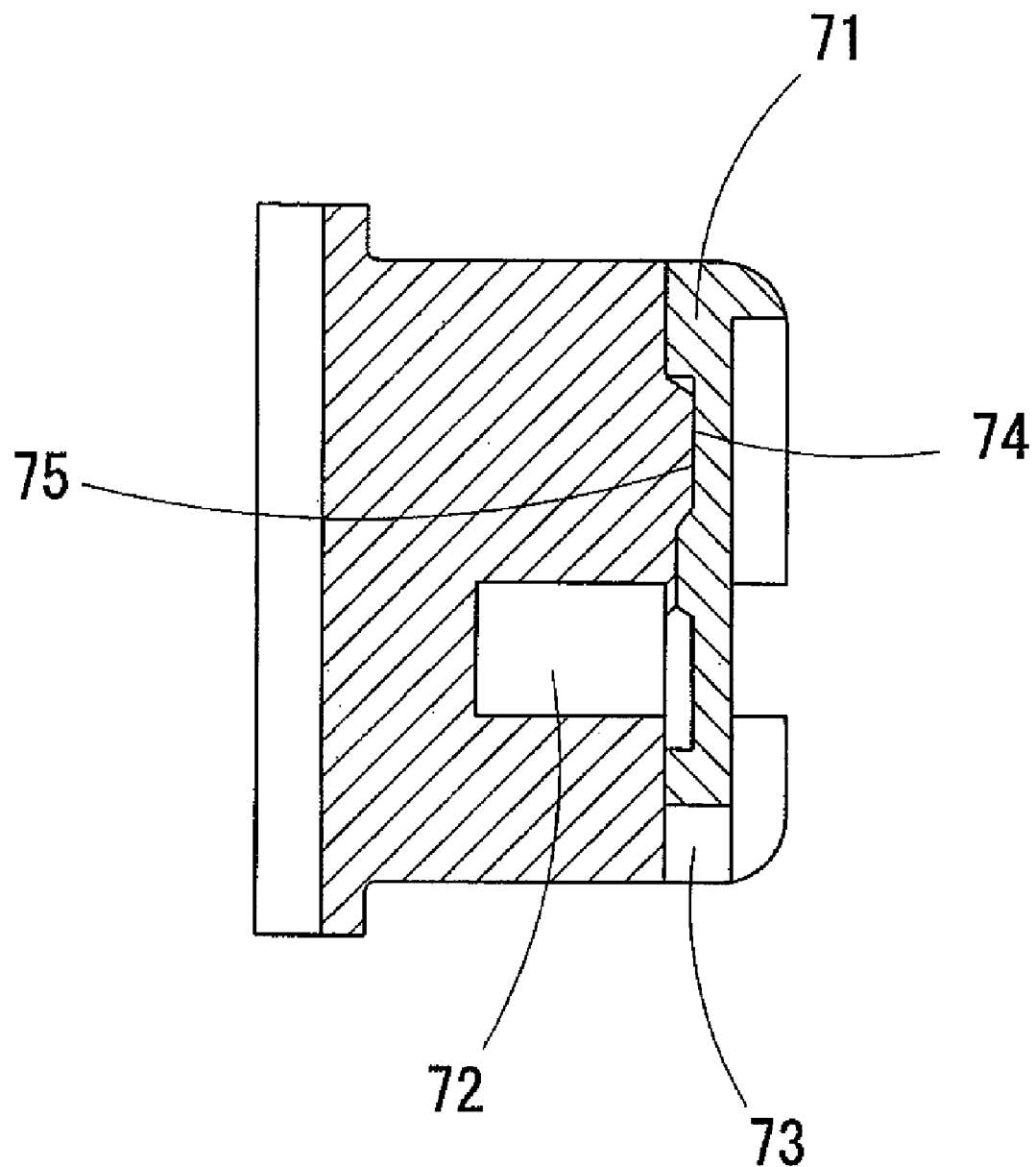
FIG. 12 is a cross-sectional view of the example of the related art shown in FIG. 11.

The direction (angle) of opening of the socket 54 is appropriately selected. The angle of opening of the socket 54 is selected depending on a desired torque or rotation. For example, as shown in FIGS. 8 to 10, the angle of inclination of an axis line L', which passes through the center of the bottom surface 54a perpendicular to the bottom surface 54a, with respect to an axis line L, which passes through the center of the base part 51 (center of the circle) and along the centerline of the joint part 53, is selected to be 0 degrees, 5 degrees or 10 degrees, for example. With such a configuration, different torque depending on the angle of opening of the socket 54 can be applied. When applying a torque to a tooth surface, if inner parts having differently angled sockets are prepared, a desired torque can be applied only by selecting the appropriate inner part without changing the bracket. Therefore, the wire can be attached in a relatively short time, and the treatment time can be reduced.

The handle part 52 is to facilitate handling of the inner part 50 and is coupled to the base part 51 by the joint part 53. The handle part 52 is used when inserting the inner part 50 into the slot 30. The handle part 52 has a width of about 8.0 mm and a length of about 7.0 mm. As described later, the handle part 52 is cut away and separated from the base part 51.

Now, assembly of the bracket 10 and the inner part 50 will be described.

Figure 6:
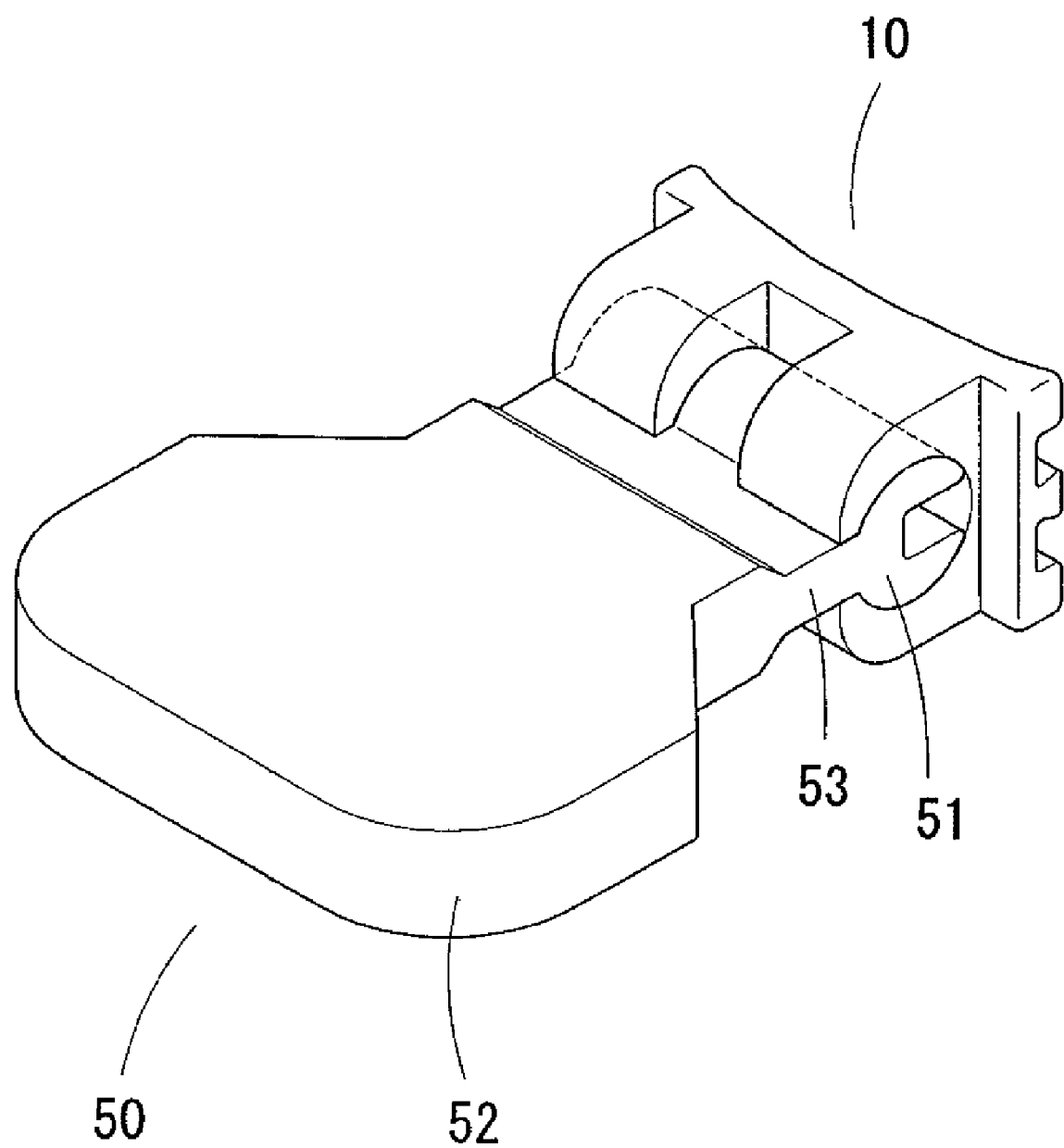
FIG. 6 is a perspective view of the inner part inserted in the bracket in the embodiment 2 of the present invention.
Figure 7:
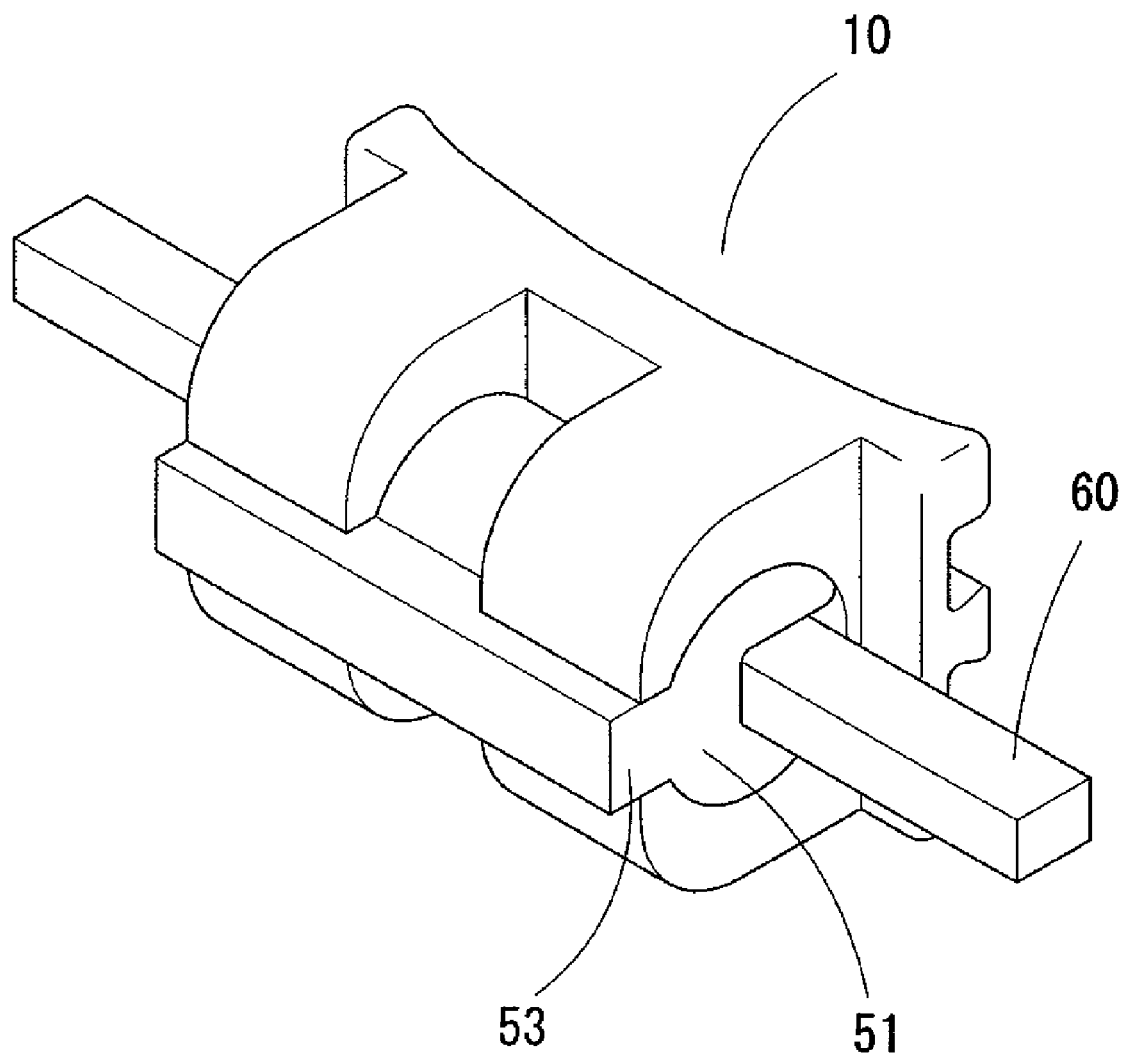
FIG. 7 is a perspective view of the inner part shown in FIG. 6 from which a base part thereof has been cut away in the embodiment 2 of the present invention.

The wire 60 having a rectangular cross section is inserted into the slot 30, and then, the inner part 50 is inserted into the slot 30. Specifically, after the wire 60 is inserted into the slot 30 through an opening 32, the inner part 50 and the slot 30 are placed side by side so that the arc-shaped outer perimeter of the inner part 50 and the arc-shaped inner surfaces (arc-shaped surfaces 12a and 13a) of the slot 30 are aligned with each other, and the opening 32 and the joint part 53 are aligned each other. Then, the inner part 50 is moved horizontally and inserted into the slot 30. When the entire inner part 50 is housed in the slot 30 as shown in FIG. 6, the handle part 52 is cut away. The inner part 50 from which the handle part 52 is removed is composed of the base part 51 and the joint part 53, and as shown in FIG. 7, the joint part 53 is positioned in the opening 32 of the slot 30 to close the opening 32. At this time, the inner part 50 (joint part 53) is held between a surface 12b of the upper arm portion 12 and a surface 13b of the lower arm portion 13 and therefore is prevented from rotating (moving) vertically, and a torque is applied to the teeth in this state.

The handle part 52 has a width of about 8.0 mm and a length of about 7.0 mm. The dimensions of the wire 60 are appropriately selected. For example, a rectangular wire having a height of 0.016 mm and a width of 0.022 mm, a height of 0.018 mm and a width of 0.025 mm, a height of 0.021 mm and a width of 0.025 mm, or a height of 0.017 mm and a width of 0.027 mm is used.

The invention claimed is:

1. An orthodontic device, comprising:
a bracket and an inner part;
wherein said bracket is adapted to be bonded to a tooth during a treatment;
wherein said bracket has a slot;
wherein said inner part has a socket;
wherein said socket has three surfaces shaped to hold a wire inserted into said socket during said treatment;
wherein said socket is further shaped to apply desired forces to said wire during said treatment;
wherein said inner part can be removed and replaced with another inner part without having to remove said bracket bonded to said tooth to realize different forces applied to said another wire; and wherein, after said wire is inserted into said socket, said inner part is rotated within said slot thereby holding said wire within said bracket.

2. The orthodontic device of claim 1, wherein said desired forces applied to said wire comprise torque.

3. The orthodontic device of claim 1, wherein said bracket and said inner part are made of either a dental metal, or a synthetic material, or a ceramic or a synthetic resin.

4. The orthodontic device of claim 3, wherein said bracket is made from a synthetic resin and said synthetic resin is either a polymethyl methacrylate, or polyoxymethylene, or polycarbonate, or polypropylene, or polyethylene or polyethylene naphthalete.

* * * * *